United States Patent
Smith

[11] Patent Number: 6,149,497
[45] Date of Patent: Nov. 21, 2000

[54] FOUNDATION GARMENT FOR THE RELIEF OF MENSTRUAL DISCOMFORT

[76] Inventor: R. Scott Smith, 235 Gulf Beach Dr. West, Saint George Island, Fla. 32328

[21] Appl. No.: 09/229,303

[22] Filed: Jan. 13, 1999

[51] Int. Cl.⁷ .................................................. A41D 27/12
[52] U.S. Cl. ........................................ 450/134; 450/155
[58] Field of Search ............................ 450/95, 124, 125, 450/126, 128, 134, 151, 155; 2/455, 464, 456, 466, 467, 228, 238, 227, 69; 128/96.1, 99.1, 100.1, 101.1, 118.1

[56] References Cited

U.S. PATENT DOCUMENTS

| | | | |
|---|---|---|---|
| 2,493,406 | 1/1950 | Hicks, III | 450/155 |
| 2,644,449 | 7/1953 | Champagne | 128/96.1 |
| 3,071,133 | 1/1963 | Eisen | 450/155 |
| 4,622,957 | 11/1986 | Curlee | 128/96.1 |
| 4,681,113 | 7/1987 | Coplans | 450/134 |
| 4,993,409 | 2/1991 | Grim | |
| 5,628,721 | 5/1997 | Arnold et al. | |
| 5,728,055 | 3/1998 | Sebastian | |

FOREIGN PATENT DOCUMENTS

| | | |
|---|---|---|
| WO97/2843 | 11/1997 | European Pat. Off. |
| 1 308 535 | 2/1973 | United Kingdom |

*Primary Examiner*—Gloria M. Hale
*Attorney, Agent, or Firm*—Foley & Lardner

[57] ABSTRACT

In order to reduce discomfort induced by menstruation, a panty girdle or the like type of foundation garment is provided with a distensible bladder which is arranged to apply pressure to one or both of the sacral or parasacral areas of a female body. The pressure can be varied through the manual manipulation of a squeeze pump that may be built into the waistband of the garment. The garment is additionally provided with an elastic foundation panel that is shaped and designed to reduce bloating and create a trimmer appearance.

20 Claims, 8 Drawing Sheets

FOUNDATION GARMENT FOR THE RELIEF OF MENSTRUAL DISCOMFORT

BACKGROUND OF THE INVENTION

1. Field of the Invention

The present invention relates generally to a foundation garment. More specifically, this invention relates to an inflatable foundation garment that is designed to relieve menstrual discomfort. In addition, the invention relates to a method for alleviating menstrual discomfort using a garment according to the invention.

2. Description of the Related Art

During and shortly prior to menstruation, many women suffer from pain and cramping in the pelvic area. These symptoms occur as a result of congestion in the pelvic area, which distorts the normal anatomy. Because the anatomy is distorted, normal neurovascular function is impaired which in turn contributes to the discomfort.

Although a number of girdle and the like type of garments have been proposed, one which is effective for relieving pain and cramping in the pelvic area prior to and during menstruation has not previously been specifically proposed.

SUMMARY OF THE INVENTION

It is an object of the present invention to provide a foundation garment that is effective for the relief of pre-menstrual and menstrual discomfort.

It is another object of the present invention to provide a foundation garment that conforms to and applies pressure to the sacral or parasacral areas. It is yet another object of the present invention to provide an adjustable pressing force on the sacral or parasacral areas.

It is a further object of the invention to provide a foundation garment, such as panty girdle or similar type garment, that holds a fluid bladder against the sacral or parasacral areas of a female body. It is yet a further object of the present invention to direct the force produced by expanding the fluid bladder to relieve discomfort incurred as a result of menstruation.

It is an additional object of the invention to provide a fluid bladder that conforms to the epidermal contours over the sacral or parasacral areas of a human female body. It is yet an additional object of the present invention to apply a pressing force to the sacral and parasacral areas for reducing pelvic congestion as a result of menstruation and for restoring the normal anatomy.

These and other objects and advantages of the present invention are achieved with a foundation garment for providing a therapeutic effect to at least one of the sacral and parasacral regions of a female. The foundation garment comprises a bladder adapted for applying a pressing force to at least one of the sacral and parasacral regions of the female; a fluid flow control unit in fluid communication with the bladder for adding fluid to distend the bladder and for removing fluid to collapse the bladder; and a first panel providing a reaction force adapted for directing the pressing force to at least one of the sacral and parasacral regions of the female. The bladder is adapted to be interposed between the first panel and at least one of the sacral and parasacral regions of the female.

According to the present invention, the above and other objects and advantages are also achieved by a method of alleviating menstrual discomfort. The method comprises distending a fluid bladder provided in a foundation garment for producing a pressing force; and directing the pressing force to at least one of a sacral and parasacral region of a humane female body.

BRIEF DESCRIPTION OF THE DRAWINGS

The present invention will become more clearly appreciated as a description of the preferred embodiment is made with reference to the appended drawings.

DETAILED DESCRIPTION OF THE PREFERRED EMBODIMENT

Figure 1:
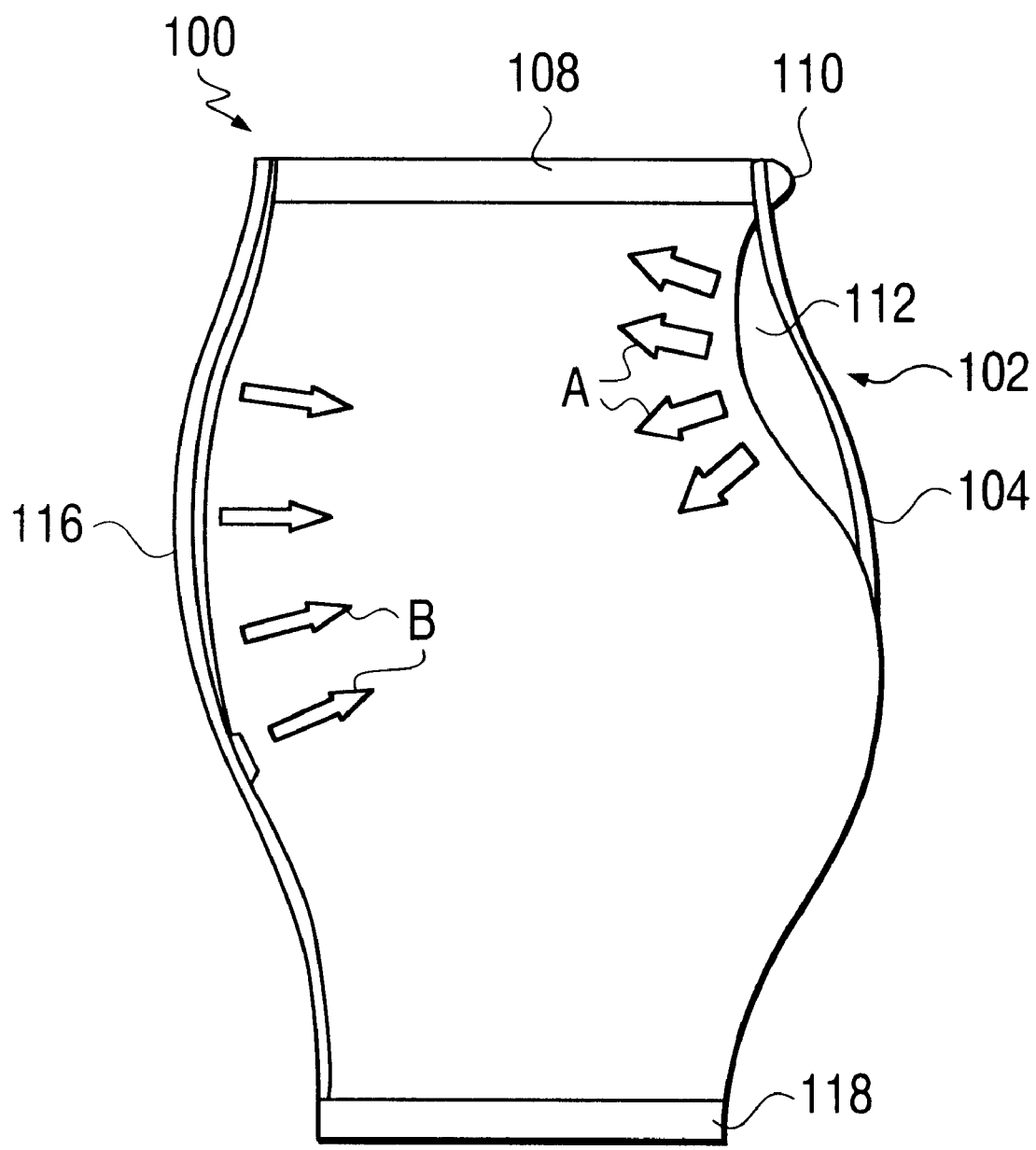
FIG. 1 is a side view of a first embodiment of the invention.
Figure 2:
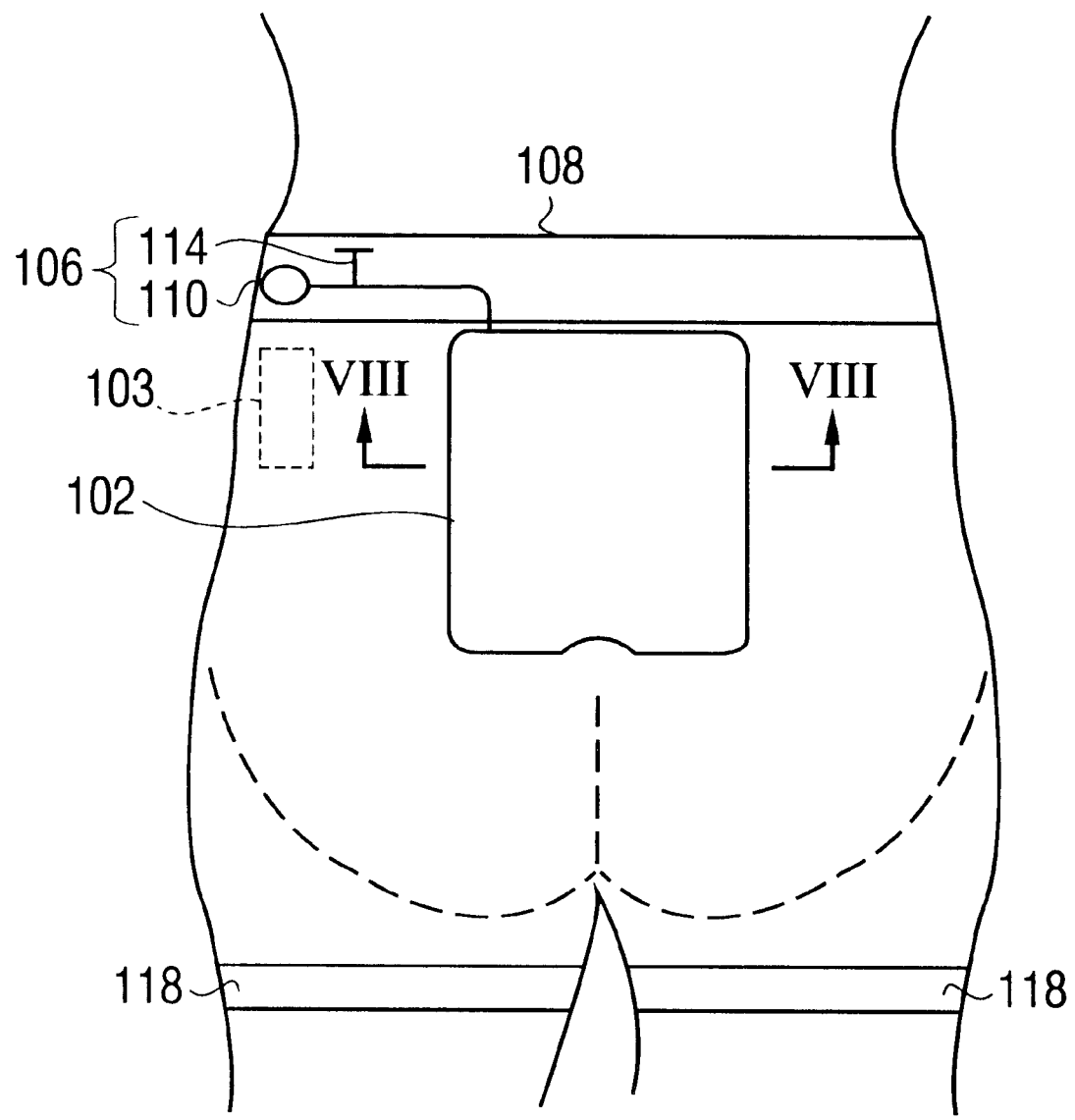
FIG. 2 is a rear elevation view showing a possible shape of the inflatable bladder shown in FIG. 1.

FIGS. 1 and 2 shows a panty girdle type foundation garment 100 according to the present invention. The garment 100 includes a distensible pouch or bladder 102 for applying pressure to either or both of the sacral and parasacral areas of a human female's anatomy. The bladder 102 is constructed of a pliable material, such as rubber or suitable synthetic resins, such that the bladder readily conforms to the epidermal contours over the sacral and/or parasacral areas of the female's body.

The bladder 102 is interposed between the female and a panel 104 that is formed of a substantially non-stretchable material, such as nylon. The panel 104 may comprise an integral portion of a homogenous foundation garment, or a separate member securely attached to a conventional foundation garment. The panel 104 may further comprise one or more straps (not shown) for encircling the user's torso to maintain the desired position of the panel 104.

According to a preferred embodiment of the present invention, a fluid flow control unit 106 is positioned in or near a waistband 108 of the garment 100. The fluid flow control unit 106 comprises a fluid supply 110 for adding fluid to a cavity 112 in the bladder 102, and a fluid release 114 for removing fluid from the cavity 112. The fluid supply 110 may comprise a hand-operated pump (e.g., a squeeze bulb), a power operated pump, or a fluid reservoir (e.g., a compressed gas cylinder) for distending the bladder 102. According to a preferred embodiment of the invention, the fluid release 114 comprises a valve for collapsing the bladder 102. The fluid control unit 106 may additionally comprise one or more check valves (not shown) for regulating the direction of fluid flow, a pressure regulator (not shown) for establishing and/or maintaining a desired fluid pressure in the bladder 102, and a collection container (103) for holding excess fluid.

The term "fluid," as it is used according to the present invention, comprises any gas, liquid or combination thereof. It is also envisioned that materials capable of transitioning between different states of matter under common ambient conditions may also be used to distend the bladder 102. According to a preferred embodiment of the present invention, the fluid comprises air and/or water.

According to a preferred embodiment of the present invention, an elastic foundation panel 116 is located on the opposite side of the garment 100 with respect to the panel 104, i.e., over the lower abdominal area of a female's body. This panel 116 produces a force "B" in a direction that is designed to reduce bloating and create a trimmer appearance.

Elastic legbands 118 may be provided to prevent the garment 100 from riding up in response to distension of the bladder 102 and/or motion of the user.

Figure 3:
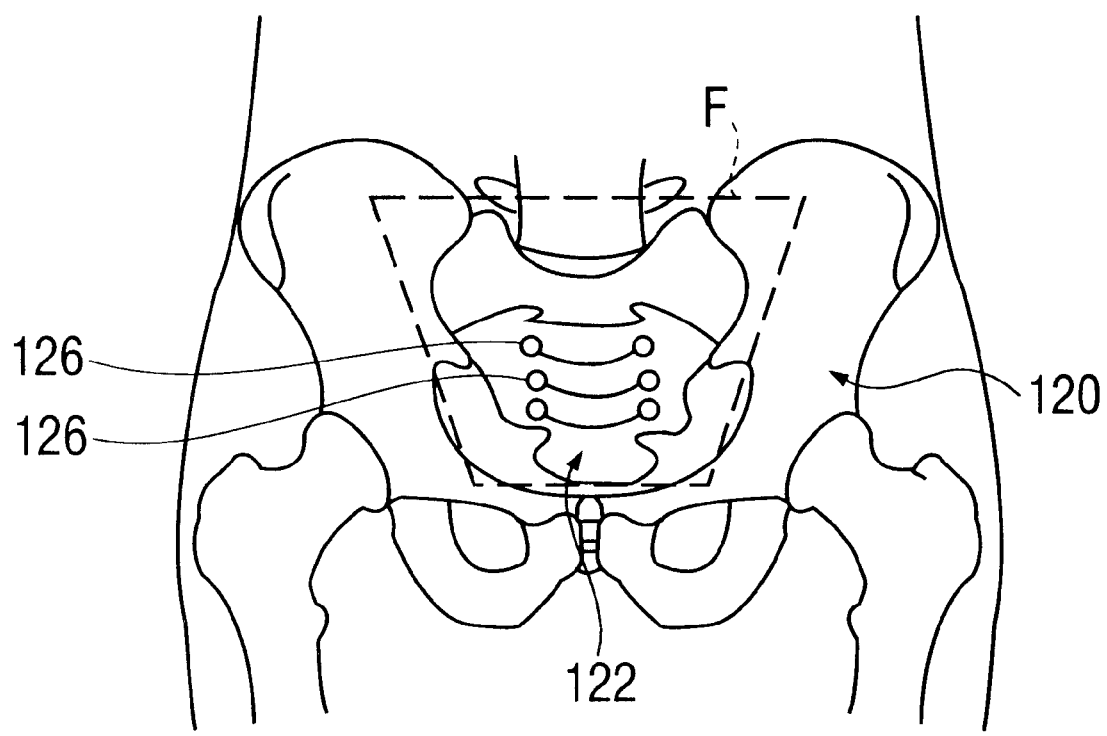
FIG. 3 is a front elevation view showing the area to which pressure is applied by an elastic foundation panel provided at the front of a garment according to the present invention.
Figure 4:
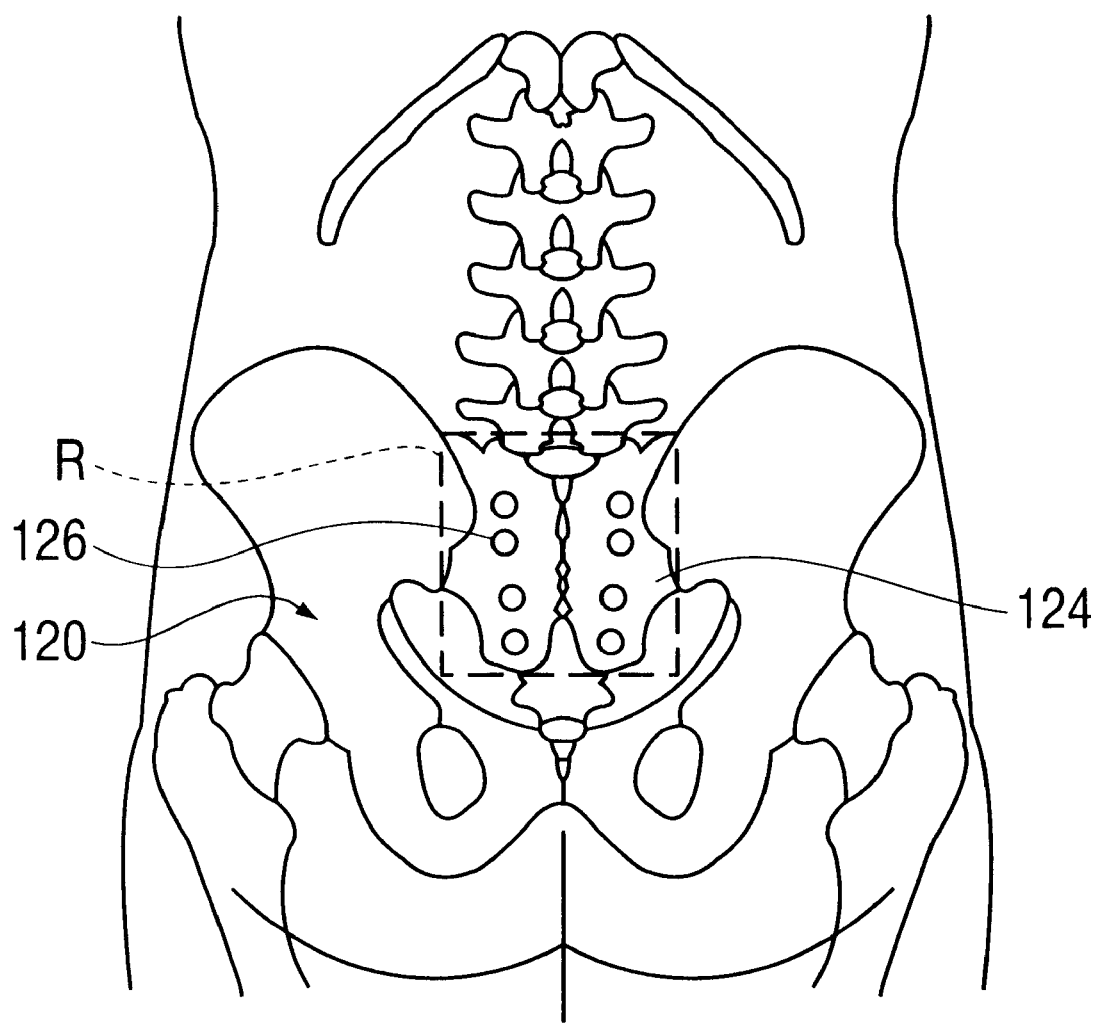
FIG. 4 is a rear elevation view showing the area to which pressure can be applied to the sacral area according to the present invention.

During menstruation, the pelvic organs and tissues become engorged with blood, which causes congestion due to edema and swelling of the entire pelvic areas 120 (see FIGS. 3 and 4). This results in pressure being placed posteriorly on the anterior sacrum 122 and sacral area 124. Nerves and veins in the sacral area 124 pass through small holes or sacral foramina 126, and the pressure that is caused by the congestion distorts the normal anatomy and impedes neurologic function and venous drainage. This change in normal venous drainage exasperates the congestion, putting even more pressure on the nerve roots and causing additional discomfort.

Figure 5:
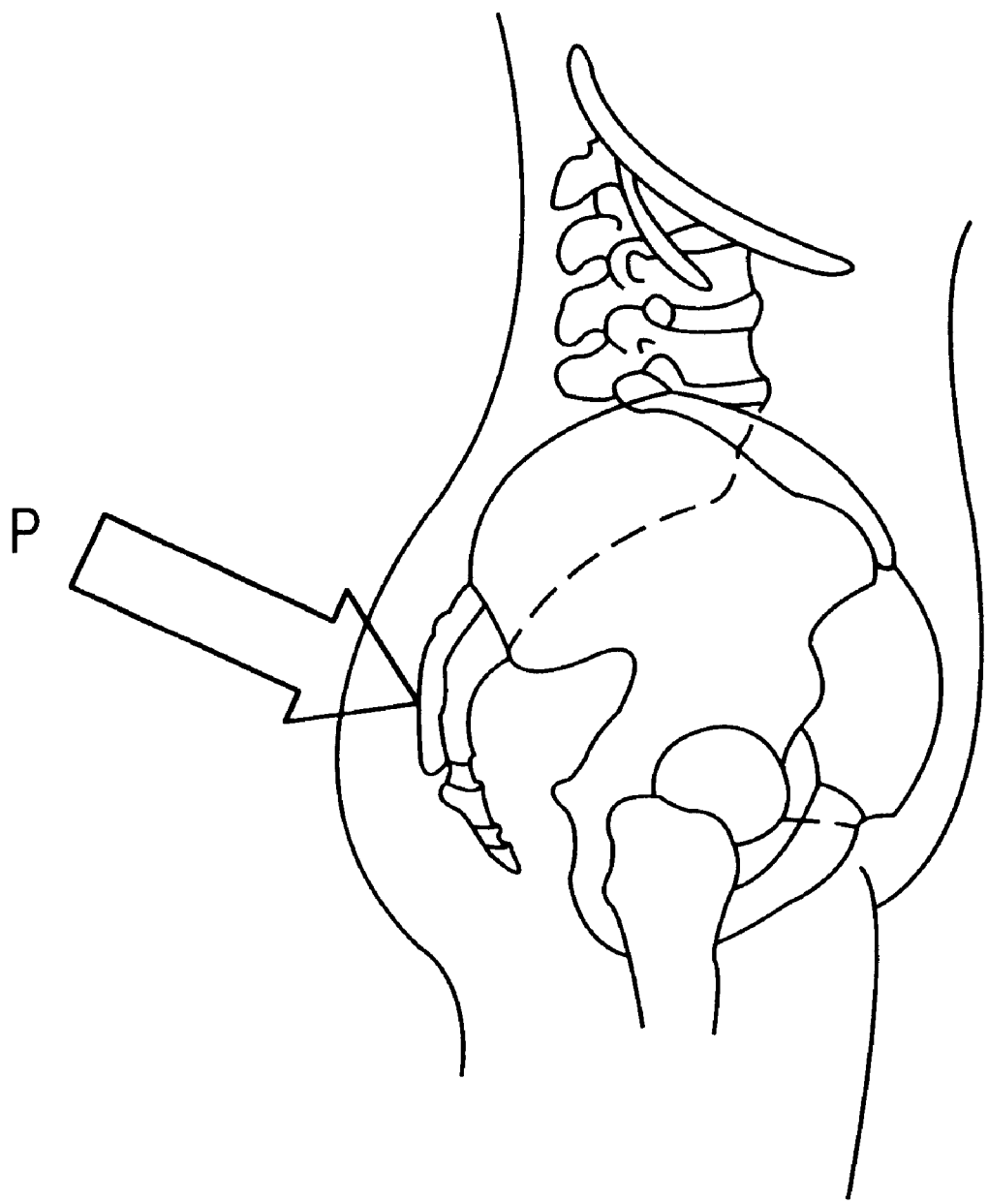
FIG. 5 is a side elevation view showing the direction in which force is applied to the sacral and/or parasacral areas.
Figure 6:
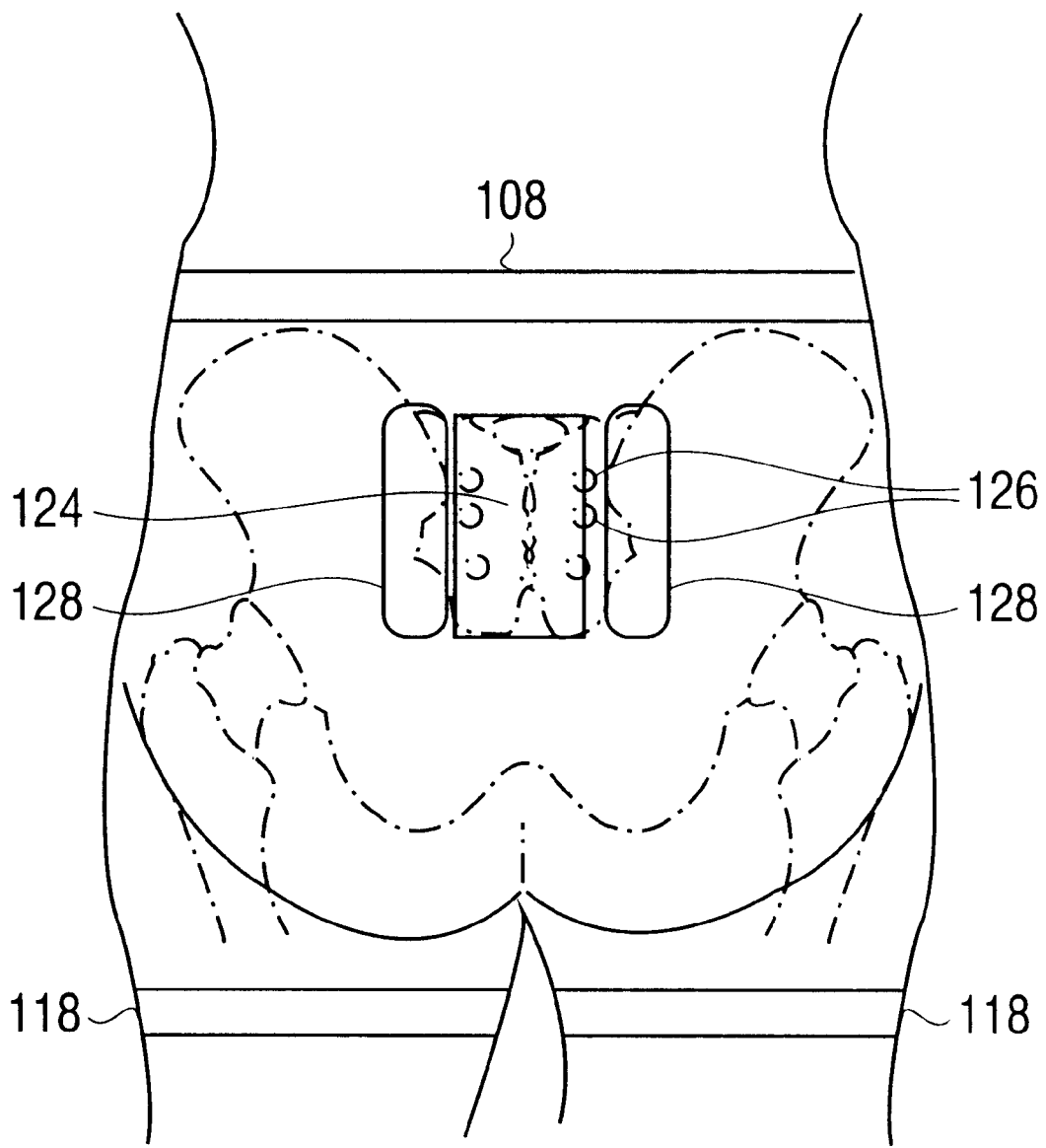
FIG. 6 is a rear elevation view showing the sacral and parasacral areas to which pressure is applied according to the present invention.

The present invention is directed to relieving the congestion and associated discomfort of menstruation by placing pressure on the posterior aspect of the sacrum and parasacral areas 124, 128 (see FIG. 6). The externally applied pressing force "P"(see FIG. 5) helps counteract the pressure that results from vascular tissue engorgement. According to the present invention, the external pressing force P places the sacrum and parasacral areas 124, 128 in a more normal anatomical relationship, which relaxes the pressure around the sacral foramina 126. This relaxation helps restore normal venous outflow and therefore helps to relieve congestion. Thus, the present invention helps to restore normal anatomy, reduces nerve irritation and decreases pain.

Figure 7:
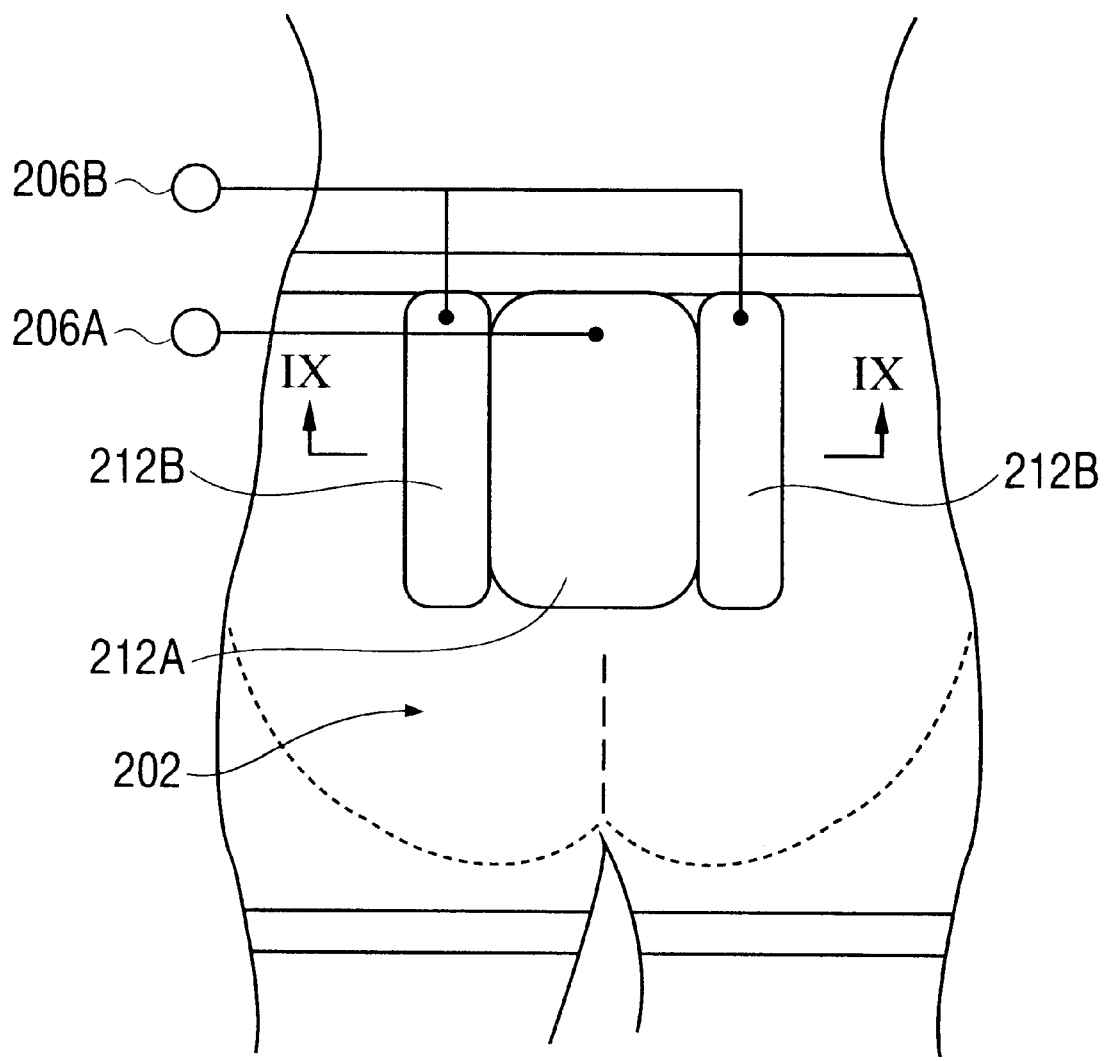
FIG. 7 is a rear elevation view showing a multiple-bladder arrangement according to a second embodiment of the invention.
Figure 9:
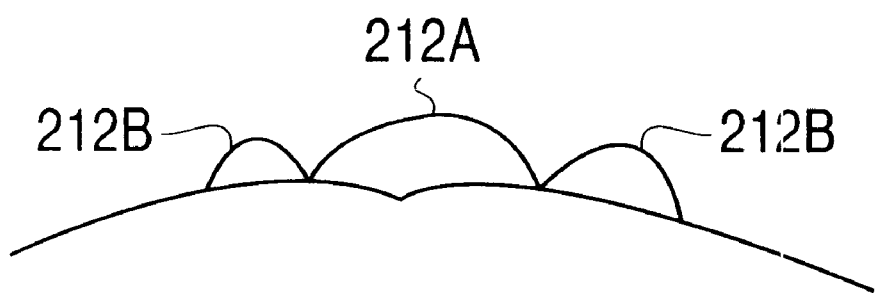
FIG. 9 is a section view taken along section line IX—IX of FIG. 7.

The present invention is not limited to the use of a single cavity bladder. According a preferred embodiment of the present invention, a multiple cavity bladder may enable different pressures to be developed in the different cavities for the comfort of the wearer. FIGS. 7 and 9 show a bladder 202 having separated sacral and parasacral cavities 212A, 212B. Two flow control units 206A and 206B respectively adjust the independent pressures in the cavities 212A, 212B. As shown in FIG. 6, the cavities 212A, 212B may apply different pressing forces to the sacral and parasacral areas 124, 128, respectively. Of course, the flow control units 206A, 206B may be combined in a single unit with appropriate valves for separately adding and removing fluid from each of the cavities 212A, 212B.

Figure 8:
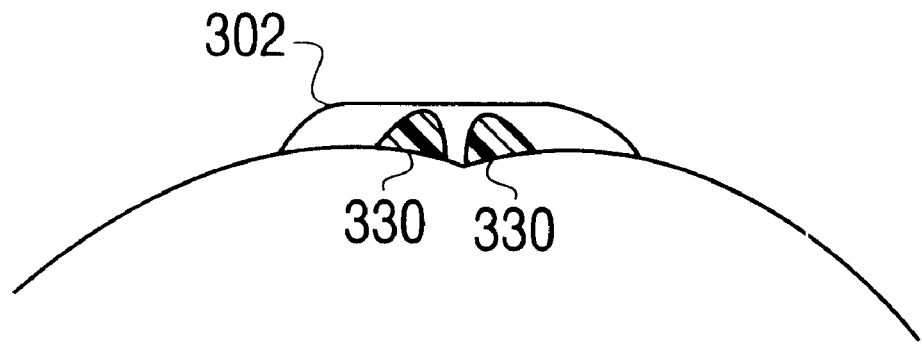
FIG. 8 is a sectional view as taken along section line VIII—VIII of FIG. 2 showing a third embodiment of the present invention wherein foam inserts are included in the bladder.

FIG. 8 shows an arrangement according to a third embodiment of the invention wherein elastomeric or foam inserts 330 are arranged within a bladder 302 to modify the pressing force that is applied the sacral area 124.

Figure 10:
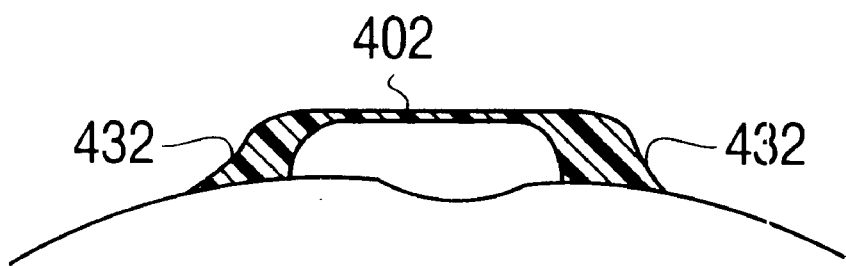
FIG. 10 is a sectional view similar to FIG. 8 showing a fourth embodiment of the invention wherein the bladder is supplemented with foam.

FIG. 10 shows a fourth embodiment of the invention. In this arrangement, foam pads 432 are located on either side of a bladder 402 in order to modify the pressing force that is applied to the parasacral areas 128.

Although references has been made to only a specific number of embodiments of the invention it will be appreciated that the invention is not restricted to these and is bound only by the appended claims.

I claim:

1. A foundation garment for providing a therapeutic effect to at least one of the sacral and parasacral regions of a female, the foundation garment comprising:

a bladder adapted for applying a pressing force to at least one of the sacral and parasacral regions of the female;

a fluid flow control unit in fluid communication with said bladder for adding a fluid to distend said bladder and for removing said fluid to collapse said bladder;

a first panel providing a reaction force adapted for directing said pressing force to at least one of the sacral and parasacral regions of the female; and an insert disposed inside said bladder, said insert being adapted for modifying the pressing force applied to at least one of the sacral and parasacral regions of the female;

wherein said bladder is adapted to be interposed between said first panel and at least one of the sacral and parasacral regions of the female.

2. The foundation garment as set forth in claim 1, wherein said bladder comprises a pliable material.

3. The foundation garment as set forth in claim 2, wherein said bladder is adapted for conforming to posterior epidermal contours over at least one of the sacral and parasacral regions of the female.

4. The foundation garment as set forth in claim 1, wherein said first panel comprises a non-stretch material.

5. The foundation garment as set forth in claim 1, further comprising:

a second panel being provided on an opposite side of the garment with respect to said first panel, said second panel comprising an elastic material adapted for reducing bloating of the female and for inducing a trimmer appearance of the female.

6. The foundation garment as set forth in claim 1, wherein said fluid flow control unit comprises a fluid supply and a fluid release for adjustably controlling fluid pressure in said bladder.

7. The foundation garment as set forth in claim 6, wherein said fluid supply comprises a hand operated pump.

8. The foundation garment as set forth in claim 7, wherein said hand operated pump comprises a squeeze bulb.

9. The foundation garment as set forth in claim 6, wherein said fluid supply comprises a power operated pump.

10. The foundation garment as set forth in claim 6, wherein said fluid supply comprises a compressed fluid cylinder.

11. The foundation garment as set forth in claim 6, wherein said fluid release comprises a valve.

12. The foundation garment as set forth in claim 11, wherein said fluid release comprises a collection container adapted for holding excess fluid.

13. The foundation garment as set forth in claim 1, wherein said garment comprise a panty girdle type foundation garment having elastic legbands.

14. A method of alleviating menstrual discomfort by providing a pressing force to at least one of the sacral and parasacral regions of a female, the method comprising the steps of:

applying to a female having menstrual discomfort, a foundation garment comprising, a pressing element adapted to exert pressure on at least one of the sacral and parasacral regions of the female; and maintaining the garment on said female for a period of time sufficient to alleviate the menstrual discomfort.

15. The method as set forth in claim 14, further comprising the steps of:

providing a fluid bladder in said foundation garment to exert said pressing force on at least one of the sacral and parasacral regions of a female;

varying fluid pressure in said bladder to adjust said pressing force.

16. A method as set forth in claim 15, wherein said varying fluid pressure includes adding fluid to inside said bladder.

17. A method as set forth in claim 15, wherein said varying fluid pressure includes removing fluid from inside said bladder.

18. A method as set forth in claim 14, further comprising:

separately varying fluid pressure in each of a plurality of independent cavities in said bladder to selectively adjust portions of said pressing force directed to different ones of said sacral and parasacral regions of said humane female body.

19. A method as set forth in claim 14, where said pressing force is applied to both of said sacral and parasacral regions.

20. A method according to claim 14, wherein said garment is applied to a female in need substantially only during times of menstrual discomfort over the course of multiple menstrual cycles.

* * * * *